United States Patent [19]

Peterson et al.

[11] Patent Number: 5,016,476
[45] Date of Patent: May 21, 1991

[54] OPTICAL FIBER BENDING STRESS PROOF TESTER

[75] Inventors: Stanley P. D. Peterson; Rudolph A. Eisentraut, both of Tucson, Ariz.

[73] Assignee: Hughes Aircraft Company, Los Angeles, Calif.

[21] Appl. No.: 385,030

[22] Filed: Jul. 25, 1989

[51] Int. Cl.⁵ .............................................. G01N 3/08
[52] U.S. Cl. ..................................................... 73/829
[58] Field of Search ................. 73/794, 796, 800, 829, 73/849, 854, 160

[56] References Cited

U.S. PATENT DOCUMENTS 3,643,497  2/1972  LeCompte ............................. 73/794
4,346,601  8/1982  France ................................... 73/829

OTHER PUBLICATIONS

France, "Novel Proof-Tester for Optical Glass Fibres", Electronics Letters, vol. 16, No. 4, Feb. 14, 1980.

*Primary Examiner*—Robert Raevis
*Attorney, Agent, or Firm*—C. D. Brown; R. M. Heald; W. K. Denson-Low

[57] ABSTRACT

An optical fiber bending stress proof tester 40 which provides multiple mandrels or roller elements 22 and 24 for applying compression and tension stresses to multiple planes on the periphery of an optical fiber 10. In one embodiment, first and second roller elements 22 and 24 are incorporated in a roller block 50 which is stable in either of two angular orientations with respect to the longitudinal axis of the fiber 10. The fiber 10 is bent in an S curve around the two rollers 22 and 24. The rollers 22 and 24 control the bend radius and therefore the stress induced in the outer fibers of the filament. In a specific extension of this embodiment, multiple sets of first and second roller elements are provided in additional roller blocks. Each block is stable in a first loading position and a second test position. In the test position, discrete planes around the entire periphery of the fiber are exposed to bending stress in a single pass through the tester. A device constructed in accordance with the teachings of the invention would effectively bend the fiber in several planes with a controlled bend radius. More significantly, the device would subject the fiber to high stress levels for a very short period of time thereby minimizing the possibility of damaging the fiber.

5 Claims, 7 Drawing Sheets

OPTICAL FIBER BENDING STRESS PROOF TESTER

BACKGROUND OF THE INVENTION

1. Field of the Invention

The present invention relates to optical fibers. More specifically, the present invention relates to techniques for testing the bending stress of optical fibers.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

2. Description of the Related Art

Certain fiber optic applications place significant demands on the tensile strength of the optical fiber. One such stressful application is in the deployment of fiber during the flight of a fiber optic guided missile. During high speed payout of optical fiber from a bobbin, the fiber is subjected to high stress at the peel point. The fiber is bent to a small radius at this peel point. The higher the velocity, the smaller the bend radius and the higher the stress. It is estimated that this bend radius is approximately 0.060" at a payout velocity of 700 feet per second.

Therefore, certain tensile and bending tests have been developed to detect flaws, nicks, cracks and other bad spots on the buffer of the fiber which would cause a fiber to break under such stress. (The tensile test is a proof test which measures the amount of tension the fiber can withstand. The bending test provides a measure of the extent to which the fiber may be bent under pressure before breakage or other damage occurs.)

One such test involves the simple application of tension to the fiber which approximates, to some degree, the stress the fiber will experience during payout. However, this test provides no measure of the bending strength of the fiber. In addition, the time at which the fiber is at high stress is too long, that is, such prolonged stress testing is known in the art cause cracks to grow, to degrade the strength of the fiber (by a phenomena known as static fatigue) and to otherwise pose the hazard of considerable and unacceptable damage to the fiber.

Another test involves the use of a mandrel. A mandrel is essentially a round shaft or pin on a bearing. The fiber is bent around the shaft or pin to provide a measure of the bending and tensile strength of the fiber. Unfortunately, this test is generally capable of testing the bending stress of the fiber in a single plane. That is, mandrel tests are not capable of testing all planes around the periphery of the fiber.

Thus, there is a need in the art for an inexpensive method and apparatus for providing high speed, nondestructive bend testing of the entire periphery of an optical fiber along its entire length.

SUMMARY OF THE INVENTION

The need in the art is addressed by the optical fiber bending stress proof tester of the present invention. The invention provides multiple mandrels or roller elements for applying compression and tension stresses to multiple planes on the periphery of an optical fiber. In one embodiment, first and second roller elements are incorporated in a roller block which is stable in either of two angular orientations with respect to the longitudinal axis of the fiber. The fiber is bent in an S curve around the two rollers. The rollers control the bend radius and therefore the stress induced in the outer fibers of the filament. In a specific extension of this embodiment, multiple sets of first and second roller elements are provided in additional roller blocks. Each block is stable in a first loading position and a second test position. In the test position, discrete planes around the entire periphery of the fiber are exposed to bending stress in a single pass through the tester.

In a second embodiment, the invention includes multiple roller elements, each mounted to apply bending stress to a specific and unique plane on the periphery of the optical fiber. This is a helical arrangement providing a single pass tester. In yet a third embodiment, the invention provides simply a set of roller elements in which one roller element is movable from a first loading position to a second test position. This embodiment provides a multiple pass tester.

A device constructed in accordance with the teachings of the invention would effectively bend the fiber in several planes with a controlled bend radius. More significantly, the device would subject the fiber to high stress levels for a very short period of time, thereby minimizing the possibility of damaging the fiber.

DESCRIPTION OF THE INVENTION

Illustrative embodiments and exemplary applications will now be described with reference to the accompanying drawings to disclose the advantageous teachings of the present invention.

Figure 1:
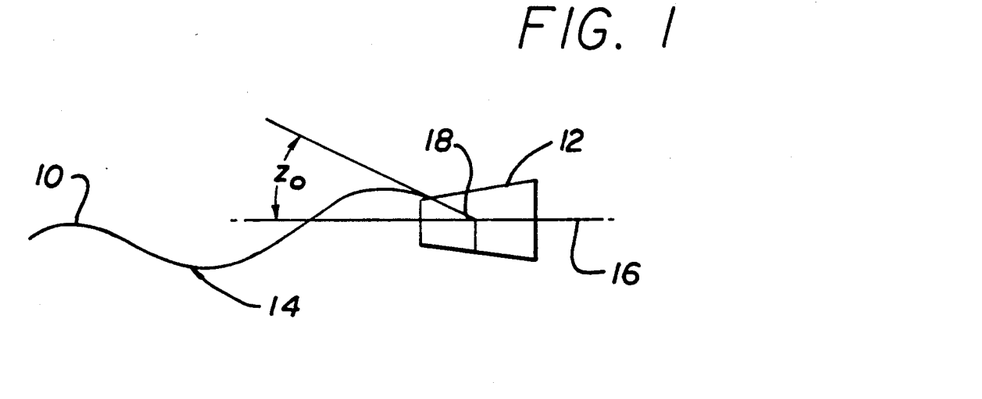
FIG. 1 is a simplified diagram of an optical fiber being payed out of a bobbin.

FIG. 1 is a simplified diagram of an optical fiber 10 being payed out of a bobbin 12. The fiber 10 pays out in a helical path 14 which is at an angle $Z_0$ of approximately 30 degrees to the longitudinal axis 16 of the bobbin 12 at the peel point. As is known in the art, during high speed payout of the fiber 10 from the bobbin 12, the fiber is subjected to high bending stress at the peel point 18. The fiber 10 is bent to a small radius at this point. The higher the velocity of the host vehicle, the smaller the bend radius and the higher the stress.

The present invention provides a proof test which simulates the bending stresses which occur during payout of the fiber 10 to insure that it will not break during payout. The present invention provides a proof test which minimizes the time the fiber is exposed to high stress levels. This is advantageous inasmuch as exposure to such high stress levels may cause cracks to grow and degrade fiber strength.

Figure 2:
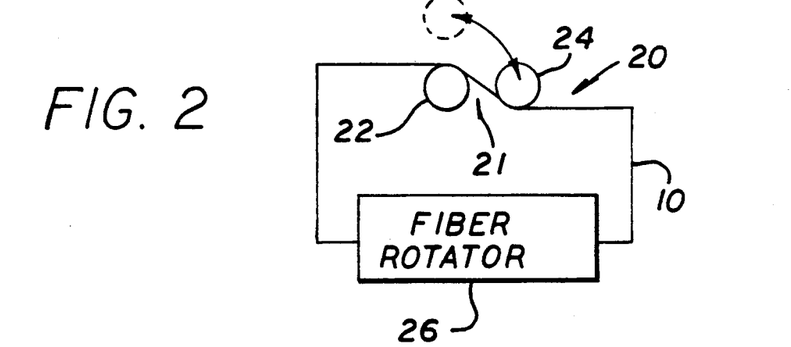
FIG. 2 is a simplified diagram of a first embodiment of a device constructed in accordance with the principles of the invention.

FIG. 2 is a simplified diagram of a first embodiment of a device 20 constructed in accordance with the principles of the invention. The device 20 includes a set 21 of two rollers 22 and 24. The first roller 22 is fixed in position while the second roller 24 is movable from a first load position shown in phantom to a second test position as shown. The fiber 10 passes in an S curve between the first and second rollers 22 and 24.

Figure 3:
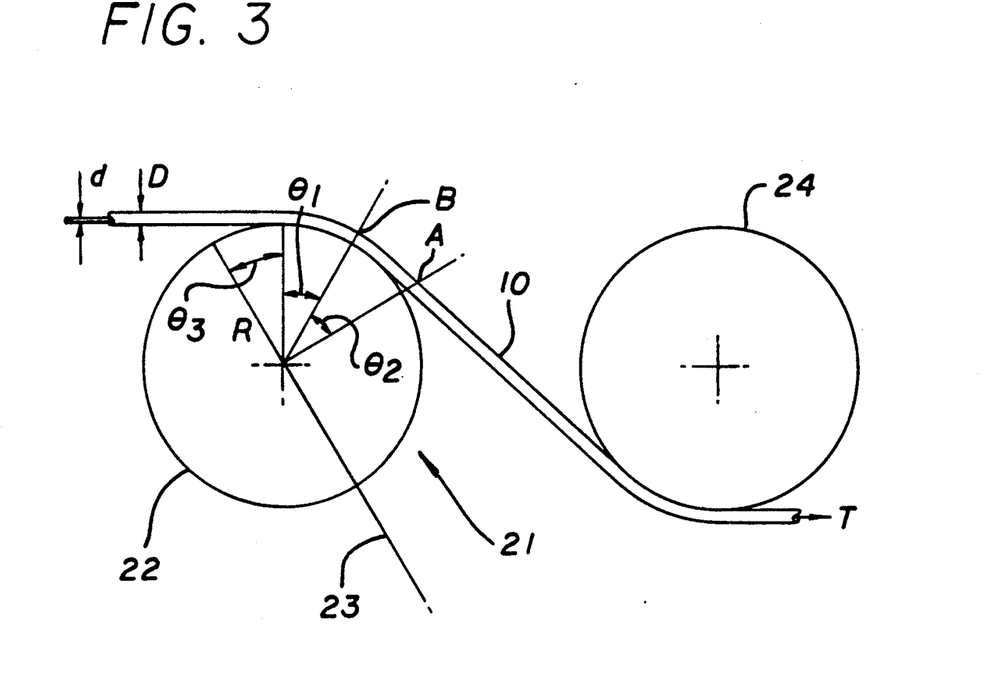
FIG. 3 is a magnified view of an optical fiber bending about a pair of rollers.

FIG. 3 is a magnified view of an optical fiber bending about a pair of rollers. As shown in FIG. 3, the contact angle $\theta_1$. As illustrated, the contact angle is preceded and followed by approach angles $\theta_2$ and $\theta_3$ with respect to an approach axis 23. The approach angle is the angular subtense between the point 'A' at which the fiber 10 begins to bend and the point 'B' at which the fiber 10 is in contact with the roller.

Returning to FIG. 2, the rollers 22 and 24 control the bend radius and therefore the stress induced in the fiber 10. The two rollers 22 and 24 subject only a portion of the surface of the fiber 10 to high tensile stresses. Accordingly, a test of the complete surface of the fiber 10 requires some mechanism for applying stress to all planes of the surface of the fiber. In the illustrative embodiment of FIG. 2, this function is performed by a fiber rotator 26. The fiber rotator 26 simply rotates the fiber 10 by one plane after each pass through the set of rollers 21. After several passes, the complete surface of the fiber 10 may be subjected to high tensile stresses. The fiber rotator 26 may be implemented by any suitable means including a toroid shaped spool (not shown) about which the fiber is wrapped. The fiber rotator 26 is driven to rotate about its longitudinal axis and about its center thus rotating the fiber 10 as it passes thereover.

Figure 4A:
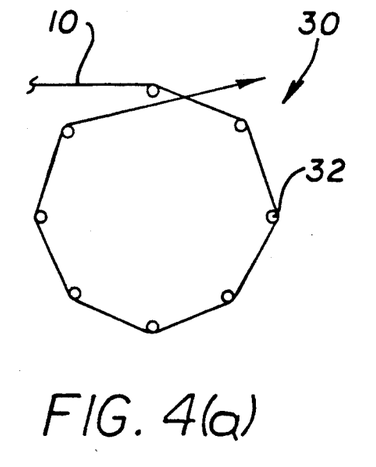
FIG. 4(a) is a first single pass alternative embodiment of a device constructed in accordance with the principles of the invention.
Figure 4B:
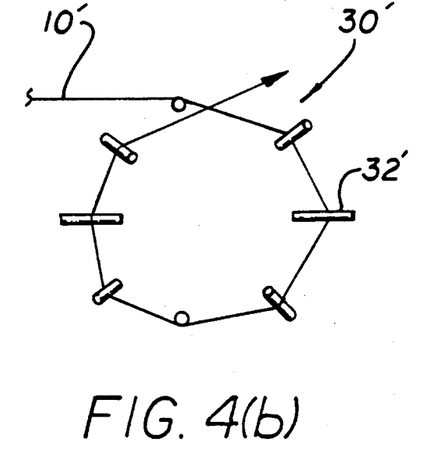
FIG. 4(b) is a second single pass alternative embodiment of a device constructed in accordance with the principles of the invention.

While the embodiment of FIG. 2 is illustrative of the present teachings, the requirement of multiple passes through the rollers 21 is a significant limiting factor on the operating speed of the device 20. The embodiments of FIGS. 4(a) and 4(b) provide single pass proof testing alternatives to the embodiment of FIG. 2. The device 30 of FIG. 4(a) includes eight rollers 32 arranged symmetrically in a circular pattern and provides for controlled bending of the fiber 10. The embodiment of FIG. 4(a), however, provides bending (tension and compression) about a single set of diametrically opposed planes. The embodiment of FIG. 4(b), on the other hand, provides bending about eight sets of diametrically opposed planes with the same number of rollers (8). The difference lies in the fact that the eight rollers 32' of the embodiment of FIG. 4(b) are oriented at a positive or negative 45 degree angle with respect to the preceding roller depending on the direction of motion, i.e., clockwise or counterclockwise.

Figures 5, 7:
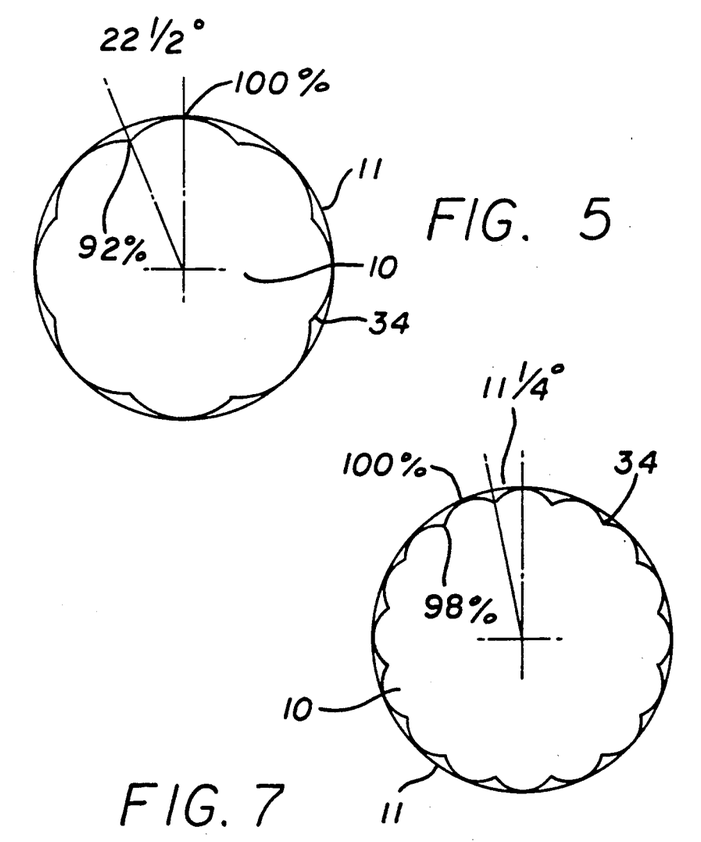
FIG. 5 shows the stress pattern on the outer surface of the fiber resulting from passing the fiber over the rollers of the device of FIG. 4(b).
FIG. 7 is a cross-sectional view of the fiber which illustrates the stress pattern on the outer surface of the fiber resulting from passing the fiber through the eight sets of rollers at 22.5 relative degrees.

FIG. 5 shows the stress pattern 34 on the outer surface 11 of the fiber 10 resulting from passing the fiber 10 over the rollers 32' of the device 30'. The maximum (100%) stress level occurs at 45 degree angles about the periphery of the fiber 10. Crack growth in glass is an exponential function of the stress level. It is therefore desirable that the stress level be controlled within safe levels. There is a concomitant need to expose the fiber to sufficient stress levels to predetermine its ability to withstand high payout stress. Accordingly, the lobing must be minimized to maintain high stress levels without exceeding safe levels for the fiber. For the embodiment of FIG. 4(b), the minimum stress level (92%) occurs at 45 degree increments offset by 22.5 degrees about the periphery 11 of the fiber 10. While the device 30' therefore applies bending stress about the complete periphery 11 of the fiber 10, it may be somewhat cumbersome and difficult to use. Accordingly, the embodiment illustrated in the schematic diagrams of FIGS. 6(a) and 6(b) constitutes a preferred embodiment of the invention.

Figure 6A:
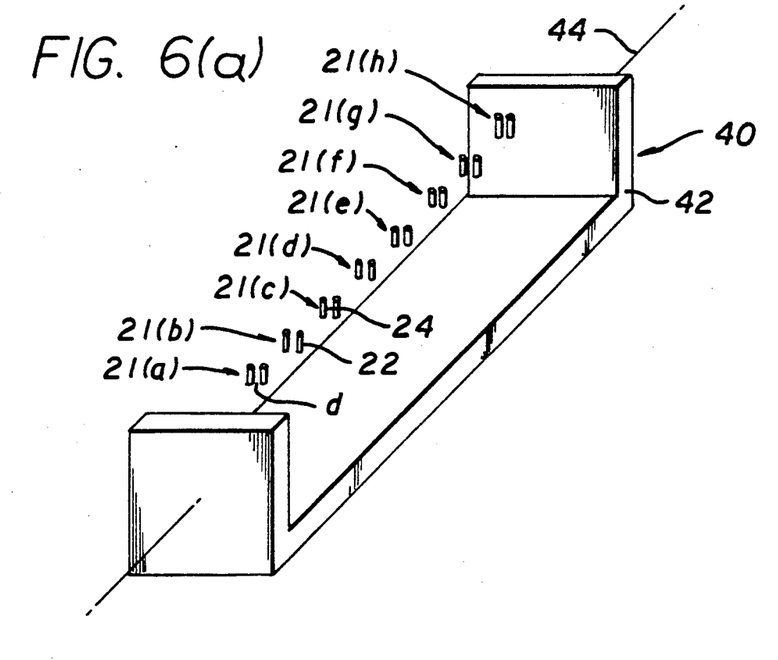
FIG. 6(a) is a schematic diagram of the preferred embodiment of the optical fiber proof tester of the present invention in a first load position.
Figure 6B:
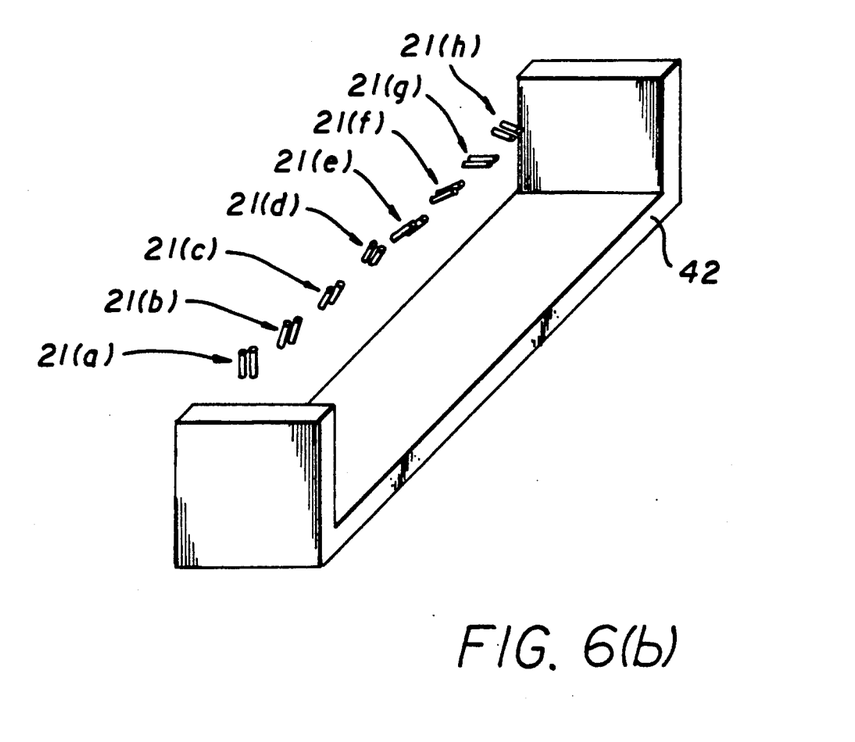
FIG. 6(b) is a schematic diagram of the preferred embodiment of the optical fiber proof tester of the present invention in a second test position.

FIG. 6(a) is a schematic diagram of the preferred embodiment of the optical fiber proof tester of the present invention 40 in a first load position and FIG. 6(b) is a schematic diagram of the preferred embodiment of the optical fiber proof tester of the present invention 40 in a second test position. The tester 40 includes a eight sets of rollers 21(a)-21(h) with each set including first and second rollers 22 and 24, respectively. In the load position of FIG. 6(a), each set of rollers is in the first load position relative to the frame 42 and the second roller 24 in each set is in a first load position relative to the first roller 22. That is, each set of rollers 21 is in a fully upright position and each roller 22 and 24 within each set 21 is in the load position shown in phantom in FIG. 2. Thus, in the load position, the rollers 22 and 24 form two parallel face-to-face rows with a small space 'd' therebetween. The space 'd' is provided to accommodate the optical fiber 10. Thus, the longitudinal axis 14 of the fiber 10 is parallel to the longitudinal axis 44 of the tester 40.

When the fiber 10 is in position, each set of rollers 21 is placed in a second test position such as that shown in FIG. 2. That is, the second roller 24 in each set 21 is moved from the first load position (face-to-face with the first roller 22) to the second test position (in rectilinear alignment with the first roller 22). Next, each set of rollers is rotated relative to the preceding set of rollers starting with the second roller 21(b). In the preferred embodiment, each set of rollers was rotated 22.5 degrees. A schematic representation of the resulting configuration is shown in FIG. 6(b).

Figure 8A:
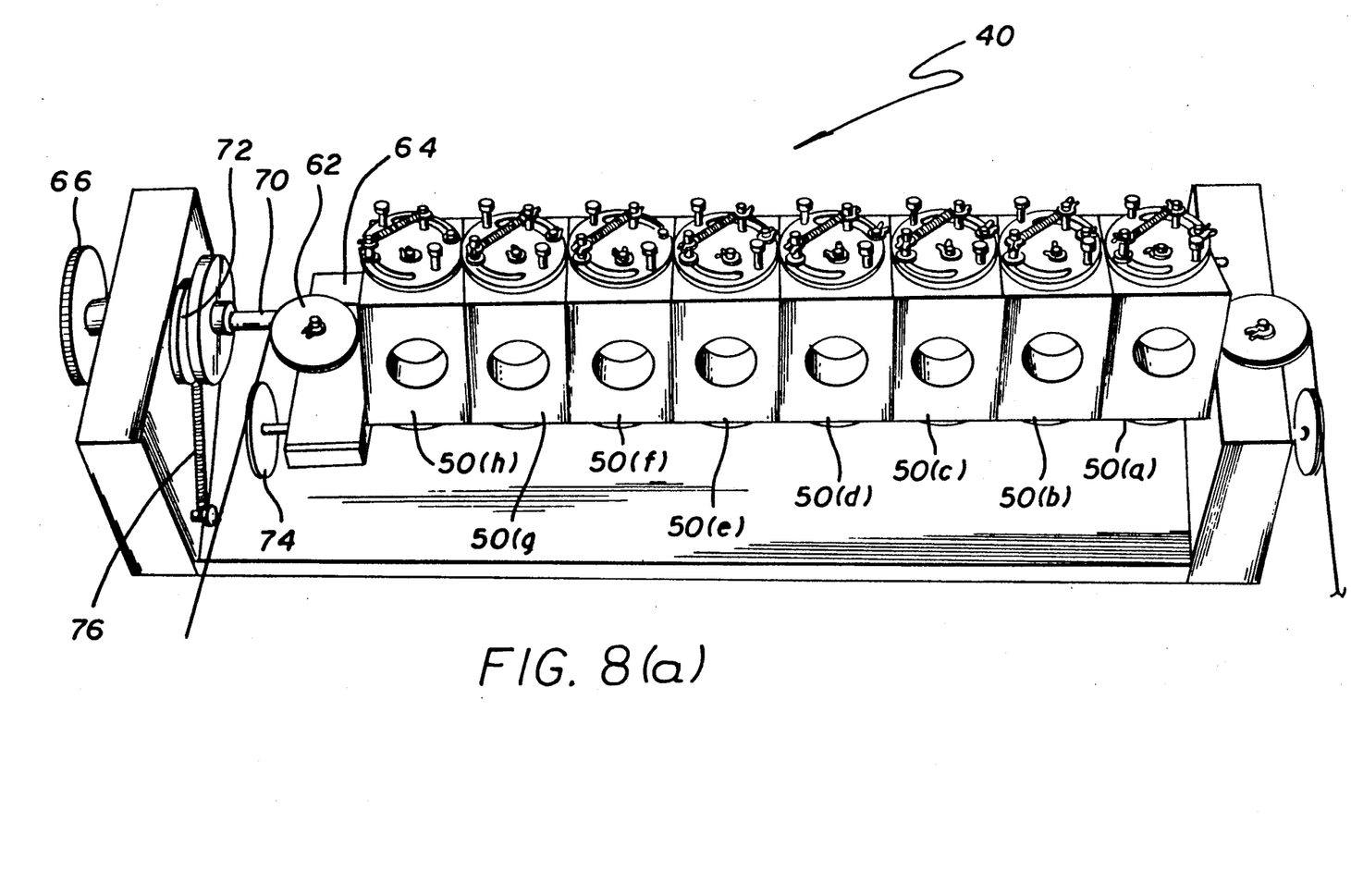
FIGS. 8(a) and 8(b) provide perspective views of the proof tester of the present invention in the first load configuration and the second test configuration, respectively.
Figure 8B:
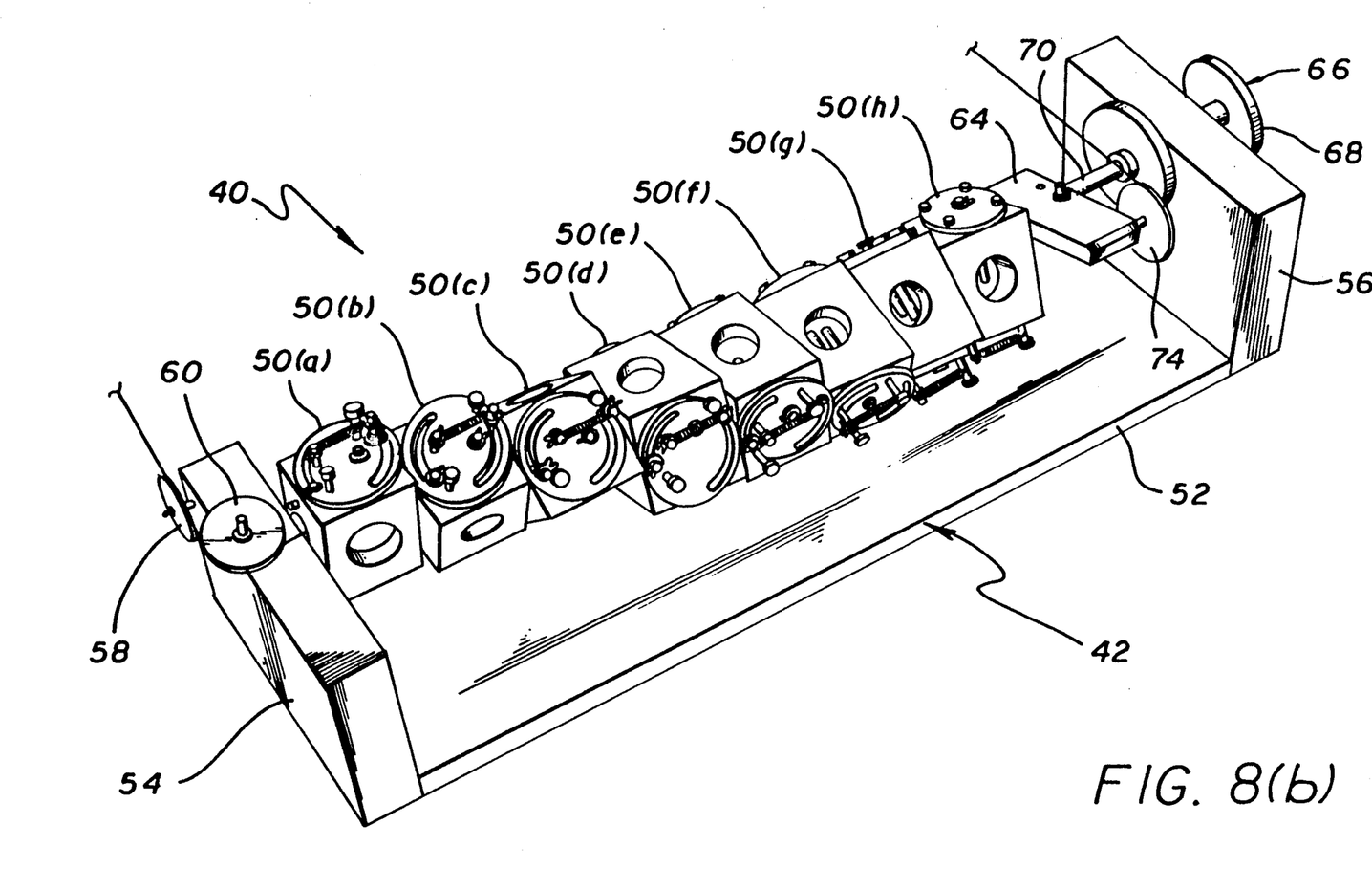

FIG. 7 is a cross-sectional view of the fiber 10 which illustrates the stress pattern on the outer surface 11 of the fiber 10 resulting from passing the fiber 10 through the eight sets of rollers 21 at 22.5 relative degrees. Note that the minimum stress point is 98% of the maximum value. Thus, in the test position, the tester 40 of the present invention provides a proof test to the complete surface of the optical fiber 10 under test. FIGS. 8(a) and 8(b) provide perspective views of the proof tester 40 of the present invention in the first load configuration and the second test configuration, respectively.

Each set of rollers 21(a)-21(h) is secured within a corresponding roller block assembly 50(a)-50(h), respectively. As illustrated in FIG. 8(b), the frame 42 of the tester 40 comprises an elongate rectangular base plate 52 and first and second support blocks 54 and 56 mounted upright at the respective ends thereof. First and second orthogonal guide pulleys 58 and 60, respectively, are mounted on the first support block 54. The guide pulleys 58 and 60 guide the optical fiber 10 into the first block assembly 50(a). A third guide pulley 62 is mounted on a pulley block 64. The pulley block 64 is attached to the last of the eight block assemblies 50(h). See FIG. 8(a). The third guide pulley 62 guides the fiber to the fourth guide pulley 74 and then from the tester 40 to a spool or bobbin not shown.

Returning to FIG. 8(b), a spring assisted crank assembly 66 is provided to rotate the tester 40 from the load position to the test position. The crank assembly 66 includes a knob 68 attached to a shaft 70. The shaft 70 extends through the second support 56 of the frame 42 and supports the crank assembly 66 thereon. On the inside of the frame 42, the shaft 70 is attached to one end of a crescent shaped cam 72. See FIG. 8(a). The spring 76 together with the crescent shaped cam 72 act as an over-center device to maintain the test position (block assemblies 50(a)-50(h)) in either the load position or the test position. The shaft 70 is attached to the last roller block assembly 50(h) through the pulley block 64.

Figures 9, 10, 11, 12, 13, 14:
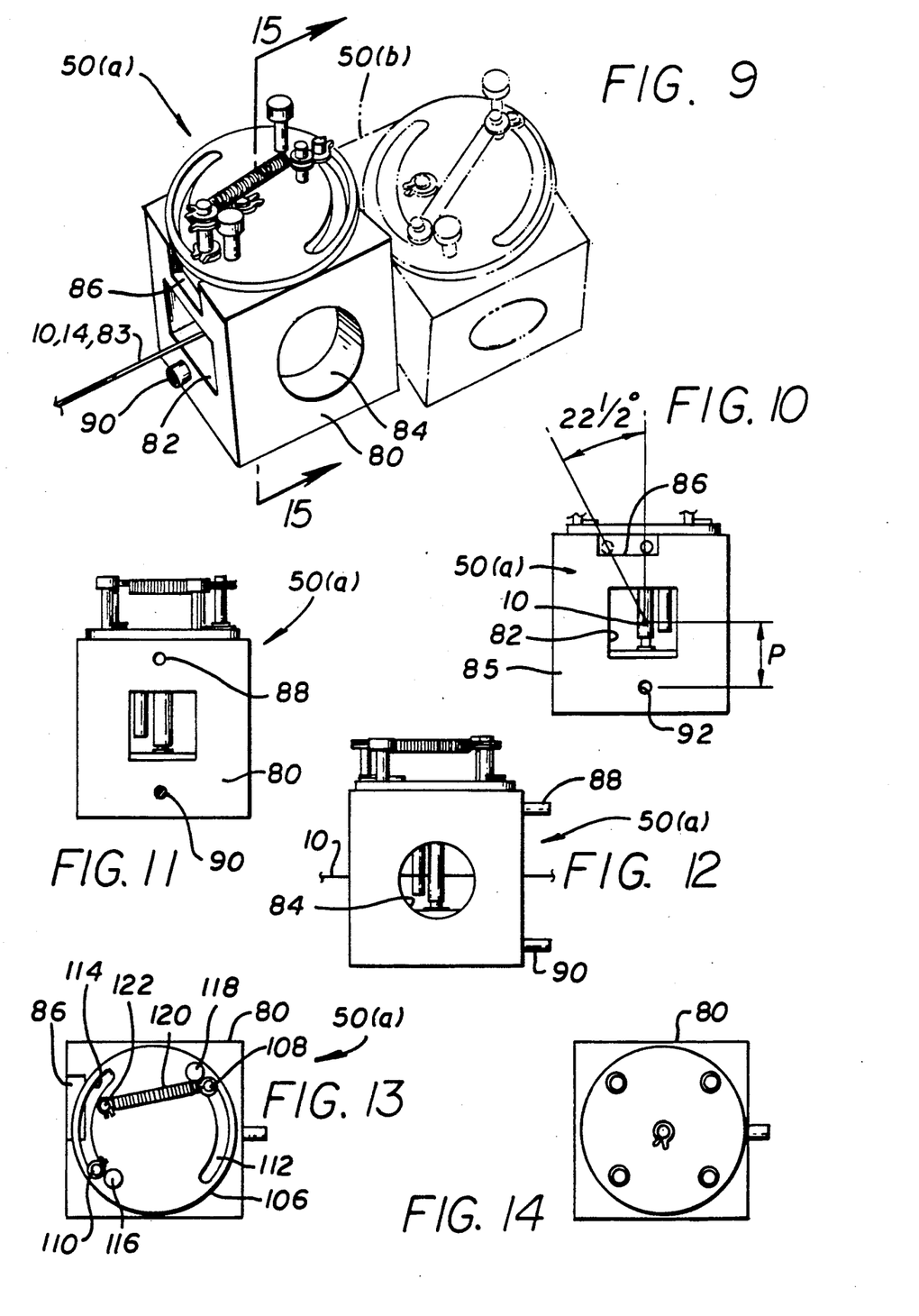
FIG. 9 is a perspective view of an individual roller block assembly with the adjacent roller block assembly shown in phantom.
FIGS. 10, 11, 12, 13, 14 and 15 provide front, rear, side, top, bottom and sectional front views of the roller block assembly of FIG. 9, respectively.

The roller block assemblies 50(a)-50(h) are of essentially identical construction and are arranged within the frame 42 in rectilinear alignment. FIG. 9 is a perspective view of an individual roller block assembly 50(a) with the adjacent roller block assembly 50(b) shown in phantom. FIGS. 10, 11, 12, 13, 14 and 15 provide front, rear, side, top, bottom and sectional front views of the roller block assembly 50(a) of FIG. 9, respectively. Each assembly 50 includes a block 80 constructed of anodized aluminum or other suitably rigid material. The block 80 has a longitudinal axis 83 which is parallel or coincident with the longitudinal axis 14 of the fiber 10. A first longitudinal opening 82 is provided through the block 50 to accommodate the fiber 10. A second opening 84 is provided transverse to the longitudinal axis 83 of the block 80 to facilitate viewing of the rollers 22 and 24. A rectangular slot 86 is provided in the front surface of the block 80. Except for the first assembly 50(a), the rectangular slot 86 cooperates with a first pin 88 protruding from the rear of the preceding block to provide for limited rotation of the block assembly 50 about pin 90 thereof. See FIGS. 10 and 11. As shown in phantom in FIG. 10, the pin 88 and hence the assembly 50 attached thereto, is limited by the walls of the slot 86 in angular excursion with respect to a pivot pin 90, extending from the rear of the previous block, which engages a hole 92 on the front surface 85 of the block 80. This limited angular excursion is effective to provide the 22.5 degree rotation of each successive assembly 50 about the fiber 10.

The degree of rotation of each assembly 50 is chosen with regard to the need to expose the entire periphery of the fiber 10 to stress and to ensure that as the fiber 10 undergoes an S bend through the rollers, it will engage the rollers of the following assembly in the appropriate position. In addition, the pivot distance 'p' between the fiber 10 and the pivot point 90, 92 must be maintained from one assembly 50 to the next to assure that after the fiber undergoes an S bend through the rollers 22 and 24 that it will enter the next set of rollers parallel to the pivot axis 90, 92.

Figure 15:
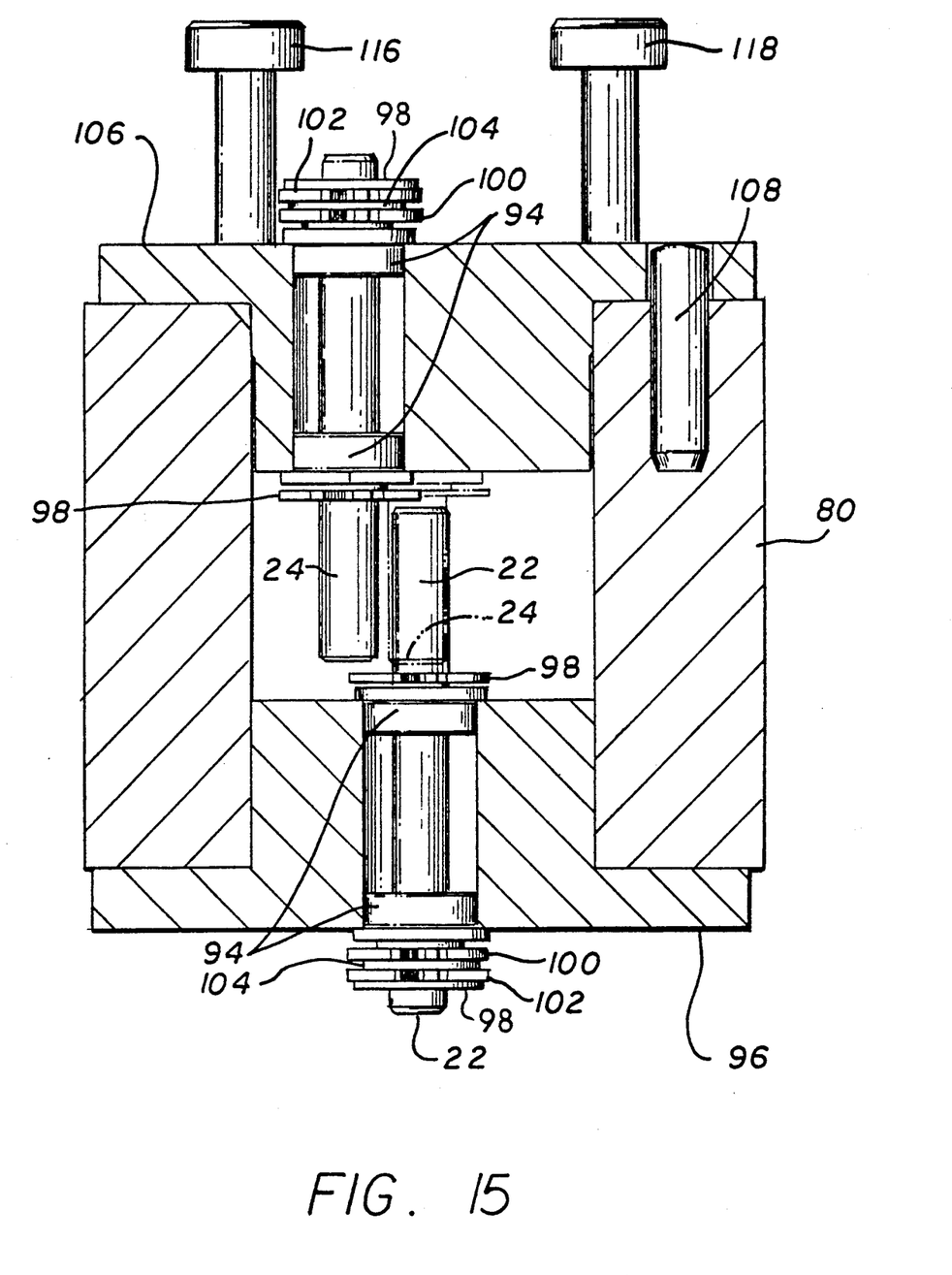

As illustrated in the sectional front view of FIG. 15, the first roller 22 is fixed within the block 80 along the centerline thereof. Each of roller 22 and 24 is ideally suspended within a smooth, high grade instrument bearing having low friction characteristics. In the preferred embodiment, the bearing is shielded and oiled rather than greased. The roller 22 is located and retained in lower plate 96 by two flanged ball bearings 94. A snap ring 98 locates the roller first snap longitudinally. A wave washer 104 is provided between two flat washers 100 and 102 to preload the bearings 94. A second snap ring 98 retains the washers and is used to adjust bearing preload. The second roller 24 is similarly located and retained within the upper rotary plate 114. The rotary plate 106 is located at the top of the block 80 as shown in FIG. 13. The rotary plate rotates 90 degrees to move the second roller 24 from the first load position to the second test position (shown in phantom in FIG. 15). The rotation of the rotary plate is limited by the movement of first and second rotation limit pins 108 and 110 in associated arcuate slots 112 and 114, respectively, in the rotary plate 106. The arcuate slots are more clearly illustrated in the top view of FIG. 13. Two shoulder screws 116 and 118 are inserted into the rotary plate 106 to facilitate the rotation thereof. A spring 120 is attached to pin 122 and the first rotation limit pin 108 to hold the rotary plate 106 in the first or second position.

In operation, the proof tester 40 of the present invention is configured in the load position of FIG. 8(a) with each movable roller 24 in each assembly 50 being in the load position. Next, the optical fiber 10 to be tested is inserted into the tester 40 between each set of rollers 22 and 24. After the fiber is threaded through the tester, it is secured to a motorized takeup spool (not shown). The second roller 24 in each block is then rotated into the test position. Then the tester knob 68 is turned to place the tester 40 in the test configuration. The motorized takeup spool is activated and the fiber is rapidly pulled through the tester 40 in a stepped spiral or helical pattern. (The radius of the helix is equal to the pivot distance 'p' between the fiber 10 and the pivot point 90, 92. See FIG. 10.) The rollers 22 and 24 provide compensating bending moments.

The contact angle of the fiber 10 on the roller is determined by the spacing between the rollers and the tension in the fiber. In the preferred embodiment, the tester was designed to provide a 30 degree contact angle so that end effects are eliminated and the full bending stress is reached as the fiber passes around each of the 16 rollers. The bend radius is determined in accordance with a stress calculation as is common in the art:

$$S = de/2R + D/2) + T/(\pi/4)d2$$

where:
S = stress,
d = glass diameter,
D = fiber diameter,
T = tension in fiber required to insure contact with rollers,
E = glass modulus,
R = roller radius, See FIG. 3. The spacing between the rollers 22 and 24 and the speed of the takeup reel determines the time of exposure to stress. Since the contact angle is small the time that the fiber is exposed to high stresses is minimized. Thus, the present invention allows the fiber to be exposed to high stresses with minimal possibility of damage to same.

The present invention has been described herein with reference to a particular embodiment for a particular application. Those having ordinary skill in the art and access to the present teachings will recognize additional modifications applications and embodiments within the scope thereof.

It is therefore intended by the appended claims to cover any and all such applications, modifications and embodiments within the scope of the present invention. Accordingly,

What is claimed is:

1. An optical fiber bending stress proof tester comprising:

first roller means for bending an optical fiber along the longitudinal axis of said optical fiber to cause tension in a first plane and compression in a second plane, diametrically opposed to said first plane, on the periphery thereof;

second roller means mounted parallel to said first roller means for bending said optical fiber along said longitudinal axis to cause tension in said second plane and compression in said first plane; and first roller block means for retaining said first and second roller means in a first or a second angular orientation with respect to the longitudinal axis of said fiber, said first roller block including pivot means for allowing said second roller means to be movable relative to said first roller means from a first loading position to a second test position at which said tension and compression stresses are exerted on the fiber and a rotary plate means having a pin and slot arrangement for providing said second roller means to be movable relative to said first roller means from a first loading position to a second test position at which said tension and compression stresses are exerted on the fiber.

2. The tester of claim 1 including first spring means for retaining the rollers in desired position.

3. The tester of claim 1 including:

third roller means for bending the optical fiber along the longitudinal axis of said optical fiber to cause tension in a third plane and compression in a fourth plane, diametrically opposed to said third plane, on the periphery thereof;

fourth roller means mounted parallel to said third roller means for bending said optical fiber along said longitudinal axis to cause tension in said fourth plane and compression in said third plane; and second roller block means for retaining third and fourth roller in said first or a third angular orientation with respect to the longitudinal axis of said fiber, said second roller block means being pivotably adjacent to said first roller block means.

4. The tester of claim 3 wherein said first roller block means includes a pin for engaging a slot in the second roller block means to support said second roller block means in said first and third angular orientations with respect to said first block.

5. The tester of claim 4 wherein said tester includes n roller block means (where n is not zero or one) each including a block for retaining two roller means in a first or an nth angular orientation respectively.

* * * * *